United States Patent [19]

Kleiner

[11] Patent Number: 4,889,661
[45] Date of Patent: Dec. 26, 1989

[54] PROCESS FOR THE PREPARATION OF AROMATIC PHOSPHORUS-CHLORINE COMPOUNDS

[75] Inventor: Hans-Jerg Kleiner, Kronberg/Taunus, Fed. Rep. of Germany

[73] Assignee: Hoechst Aktiengesellschaft, Frankfurt am Main, Fed. Rep. of Germany

[21] Appl. No.: 554,591

[22] Filed: Nov. 23, 1983

[30] Foreign Application Priority Data

Nov. 27, 1982 [DE] Fed. Rep. of Germany ....... 3244031

[51] Int. Cl.$^4$ .............................................. C07C 5/02
[52] U.S. Cl. .................... 562/815; 562/818; 562/819
[58] Field of Search ...................... 260/543 P

[56] References Cited

U.S. PATENT DOCUMENTS 3,244,745  4/1966  Toy et al. .................. 260/543 P

FOREIGN PATENT DOCUMENTS 0093420  4/1983  European Pat. Off. .

OTHER PUBLICATIONS

Houben-Weyl *Methoden der Organischen Chemie*, Band XII/1, (1963), Georg Thieme, Publ. Stuttgart. *Organische Phosphorverbindungen*, Pt. 1 K. Sasse at page 129.
Derwent Abstracts 51,340 K/21, (Russian 943,243 dtd Jul. 15, 1982).

Kosolapoff, G. M. et al. *Organic Phosphorus Compounds* (1973) vol. 4 at p. 95. Wiley-Interscience, Publ.
Kosolapoff, Gennady M. Organophosphorus Compounds (1958), John Wiley & Sons, Publ. pp. 59-60.

*Primary Examiner*—Paul J. Killos
*Attorney, Agent, or Firm*—Curtis, Morris & Safford

[57] ABSTRACT

Aromatic phosphorus-chlorine compounds, especially diphenylphosphinyl chloride $(C_6H_5)_2P(O)Cl$, phenylphosphonyl dichloride $C_6H_5P(O)Cl_2$, dichlorophenylphosphine $C_6H_5PCl_2$ and chlorodiphenylphosphine $(C_6H_5)_2PCl$, and the corresponding sulfur analogs, are obtained by reaction of aromatic phosphorus compounds, which contain oxygen or sulfur, of the formula I

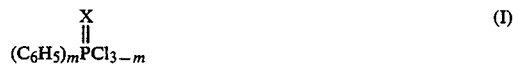

in which X=O or S, and m=1, 2 or 3, with phosphorus-chlorine compounds of the formula II

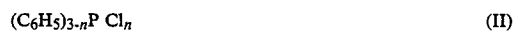

in which n=1, 2 or 3, at temperatures between about 330° and 700° C. Preferred starting materials are triphenylphosphine oxide $(C_6H_5)_3PO$ and phosphorus trichloride $PCl_3$.

The reaction products are mainly intermediates in a variety of special areas, such as the pharmaceuticals, plant-protection, dye and polymer sectors.

6 Claims, No Drawings

PROCESS FOR THE PREPARATION OF AROMATIC PHOSPHORUS-CHLORINE COMPOUNDS

Aromatic phosphorus-chlorine compounds, such as, for example, diphenylphosphinyl chloride $(C_6H_5)_2P(O)Cl$, phenylphosphonyl dichloride $C_6H_5P(O)Cl_2$, phenylthiophosphonyl dichloride $C_6H_5P(S)Cl_2$, dichlorophenylphosphine $C_6H_5PCl_2$, chlrodiphenylphosphine $(C_6H_5)_2PCl$, etc., are mainly intermediates in various special fields, such as the pharmaceuticals, plant-protection, dye and polymer sectors.

These compounds can be prepared by a number of known methods. Thus, for example, diphenylphosphinyl chloride $(C_6H_5)_2P(O)Cl$ can be obtained in a conventional manner from diphenylphosphinic acid $(C_6H_5)_2P(O)OH$ which, in turn, is accessible by alkaline decomposition of triphenylphosphine oxide $(C_6H_5)_3PO$; the latter (triphenylphosphine oxide) is an industrial waste product which is produced in not inconsiderable amounts, especially in the so-called Wittig reaction.

Phenylphosphonyl dichloride $C_6H_5P(O)Cl_2$ can be obtained, inter alia, by phosgenation of phenylphosphonic diesters $C_6H_5P(O)(OR)_2$, in which R=organic radical; phenylphosphonic diesters are, in turn, accessible, for example, by reaction of bromobenzene with trialkyl phosphites in the presence of nickel bromide.

Phenylthiophosphonyl dichloride $C_6H_5P(S)Cl_2$ is obtained, for example, by sulfuration, starting from dichlorophenylphosphine C6H5PCl2.

Dichlorophenylphosphine $C_6H_5PCl_2$ and chlorodiphenylphosphine $(C_6H_5)_2PCl$ are produced, for example, by the method of K. Sommer (Zeitschrift für anorganische und allgemeine Chemie, 376 (1970) p. 39) together by reaction of triphenylphosphine $(C_6H_5)_3P$ with phosphorus trichloride $PCl_3$ at temperatures around 280° C. under pressure, optionally with the addition of $AlCl_3$ as a catalyst. Moreover, it has already been proposed (Patent Application P 3,216,381.9-HOE 82/F 086) to prepare dichlorophenylphosphine and chlorodiphenylphosphine by reacting triphenylphosphine and phosphorus trichloride at temperatures between 320° and 700° C., the process advantageously being carried out under elevated pressure in the temperature range between 320° and 500° C., and under normal pressure in the temperature range between about 500° and 700° C.

Although at least some of the processes of the state of the art for the preparation of aromatic phosphorus-chlorine compounds are quite useful processes (such as, in particular, that for the preparation of dichlorophenylphosphine and chlorodiphenylphosphine in accordance with Patent Application P 3,216,381.9-HOE 82/F 086), the starting materials necessary for them are not always accessible easily and at low cost.

With the object of improving the processes of the state of the art for the preparation of aromatic phosphorus-chlorine compounds, especially in respect of the choice of starting materials which are easier to obtain and of lower cost, it has now been found that this aim is achieved by reacting triphenylphosphine oxide or sulfide with phosphorus trichloride and reacting the primary products resulting from this reaction.

Thus the invention relates to a process for the preparation of aromatic phosphorus-chlorine compounds which comprises reacting aromatic phosphorus compounds which contain oxygen or sulfur—denoted phosphine oxides or sulfides in the following text—of the formula I:

$$(C_6H_5)_mPCl_{3-m} \quad \text{with } X \text{ double bonded to P} \tag{I}$$

in which X=O or S, preferably=O and m=1, 2 or 3, with phosphorus-chlorine compounds of the formula II $$(C_6H_5)_{3-n}PCl_n \tag{II}$$

in which n=1, 2 or 3, at temperatures between about 330° and 700° C.

The phosphine oxides and sulfides included in the formula I contain at least one phenyl radical bonded to the phosphorus; the compounds are as follows:

for X=O when
 m=3: triphenylphosphine oxide $(C_6H_5)_3P=O$
when
 m=2: diphenylphosphinyl chloride

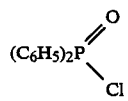

when
 m=1: phenylphosphonyl dichloride

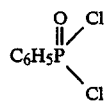

for X=S when
 m=3: triphenylphosphine sulfide $(C_6H_5)_3P=S$
when
 m=2: diphenylthiophosphinyl chloride

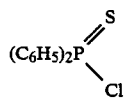

when
 m=1: phenylthiophosphonyl dichloride

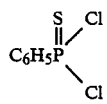

Preferred compounds I are those with X=O (phosphine oxides). A particularly preferred compound I is triphenylphosphine oxide $(C_6H_5)_3PO$; this compound is an industrial waste product which is produced in considerable quantity (particularly in the Wittig reaction).

The other compounds of the formula I with X=O and m=2 and m=1 can then be obtained, inter alia, by the reaction according to the invention of triphenylphosphine oxide with phosphorus trichloride.

Triphenylphosphine sulfide $(C_6H_5)_3PS$ is accessible, for example, by sulfuration of triphenylphosphine in a known manner. The compounds of the formula I with X=S and m=2 and m=1 can be obtained in a manner analogous to the corresponding oxygen compounds, for example, by the reaction according to the invention of triphenylphosphine sulfide with phosphorus trichloride.

The phosphorus-chlorine compounds included in formula II are as follows:
when n=3: phosphorus trichloride $PCl_3$
when n=2: dichlorophenylphosphine $C_6H_5PCl_2$
when n=1: chlorodiphenylphosphine $(C_6H_5)_2PCl$.

The preferred compound II is phosphorus trichloride $PCl_3$; it is a known commercial product which is available in large quantities. For the reaction according to the invention, it is advantageous to use the phosphorus trichloride in the freshly distilled form.

While the compounds of the formula II with n=2 and n=1 can, as mentioned in the introduction, be obtained, for example, by reaction of triphenylphosphine with phosphorus trichloride, it is more favorable to prepare them from triphenylphosphine oxide and phosphorus trichloride in the manner according to the invention.

In order to carry out the process according to the invention, the phosphine oxides or sulfides I and the phosphorus-chlorine compounds II are advantageously employed in a molar ratio of about 1:1 to 4. However, excesses of, for example, compounds I and excesses of compounds II above the molar ratio of, for example, 1:4 are likewise possible.

In the lower part of the temperature range in the process according to the invention—at about 330° to 500° C.—temperatures between about 360° and 460° C. are preferred.

This process variant is preferably carried out under superatmospheric pressure, in particular under the (autogenous) pressure set up in a closed reaction vessel (between about 5 and 100 bar as a rule).

In this instance, the reaction time is always between about 1 and 80 hours, the shorter reaction times being advantageous at the higher temperatures and the longer reaction times at the lower temperatures.

In the upper part of the temperature range in the process according to the invention—at about 500° to 700° C.—the preferred temperatures are between about 500° and 600° C.

This process variant is preferably carried out under normal pressure and advantageously such that the mixture of the phosphine oxide or sulfide of the formula I with the P-Cl compound of the formula II, which mixture has, where appropriate, been heated to about 60° C. to improve the solubility, is metered, using a metering device, into the reaction zone heated to the reaction temperature (for example an electrically heated tube). It can also be advantageous during this to pass through a stream of gas which does not react with the starting materials and final products (for example nitrogen, argon, but also hydrogen chloride etc.).

In this instance, the reaction times are, in practice, of the order of only seconds.

The two process variants mentioned above, which are suitable for both discontinuous and continuous operation, are worked up, as a rule, by distillation.

Moreover, various metal compounds can be added as catalysts in both process variants. For example, the halides, carbonates, acetates etc. of the following metals: alkali metals, alkaline earth metals, aluminum, tin, lead, copper, silver, iron, cobalt, nickel etc. are suitable for this. Lead, copper, silver and nickel compounds are preferred.

The amount of catalyst is normally between about 0.1 and 2% by weight, preferably between about 0.3 and 0.8% by weight, relative to the phosphine oxide or sulfide of the formula I which is used.

Normally, the process according to the invention provides a mixture of various aromatic P-Cl compounds which can be separated by distillation. As a rule, the main products produced are the phosphorus derivatives formed from the phosphine oxides or sulfides of the formula I by replacement of one and, when present, two phenyl groups by chlorine, and the phosphorus compounds formed from the P-Cl compounds of the formula II by replacement of a chlorine atom by the phenyl group:

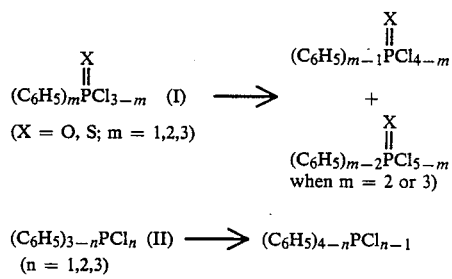

In the preferred case where triphenylphosphine oxide is used as starting compound I and phosphorus trichloride is used as starting compound II, this means that the main products formed are diphenylphosphinyl chloride, phenylphosphonyl dichloride and dichlorophenylphosphine:

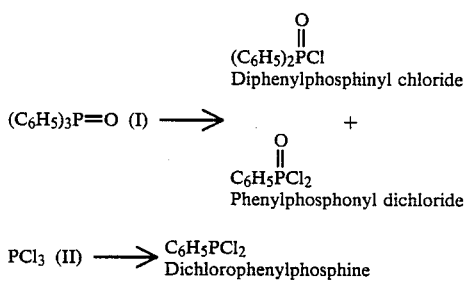

The molar ratio of the starting materials, the particular temperature and pressure conditions and the reaction time and, where appropriate, the catalyst used have a not inconsiderable effect on the composition of the reaction product.

The formation of a mixture of products in the process according to the invention is explained by the reaction products initially formed from the starting compounds I and II being able in turn to react again with the starting materials; the products thus formed can then, where appropriate, again react with the original starting materials or with the original final products etc. The following list of what are probably the most important of the rather wide variety of possible reactions should make the mixture of compounds produced in the process according to the invention understandable:

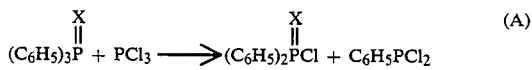

-continued

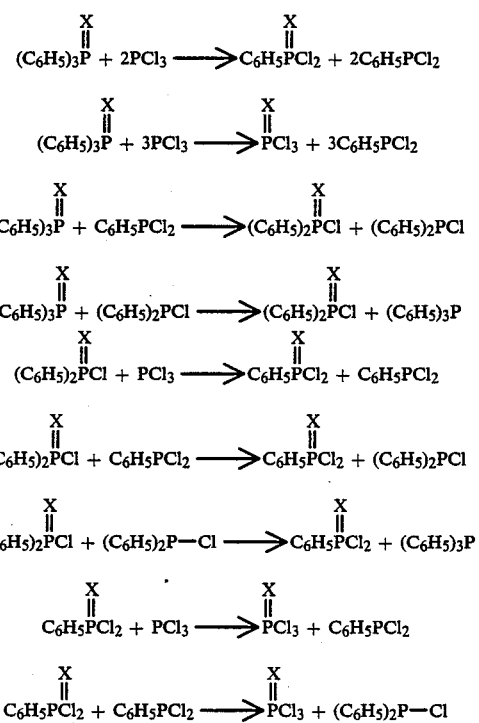

(B)
(C)
(D)
(E)
(F)
(G)
(H)
(I)
(J)

The invention represents a considerable advance in this area, in particular because of the possibility of producing, in a simple manner, from the industrial waste product triphenylphosphine oxide $(C_6H_5)_3PO$, which otherwise can hardly be utilized in a worthwhile manner, using the process according to the invention, a number of valuable aromatic P-Cl compounds, in particular diphenylphosphinyl chloride, phenylphosphonyl dichloride, dichlorophenylphosphine and chlorodiphenylphosphine.

The success of the reaction according to the invention was extremely surprising because, in fact, hardly any, or at least only very few, reactions of the rather unreactive triphenylphosphine oxide (and sulfide) in which the phenyl group can be replaced in a defined manner by other groups, have been known hitherto. In any event, reactions of triphenylphosphine oxide and sulfide comparable with the reaction according to the invention have not hitherto been described. Furthermore, it was surprising that, using the process according to the invention, a hardly utilizable mixture of a large number of compounds, each in only small amounts, as could be assumed on the basis of the wide variety of possibilities of further reaction of the primary reaction products (see equations A to J above), is not produced, on the contrary only two or three aromatic P-Cl compounds are virtually always produced as the main products and other secondary products are only obtained in minor amounts, some of them very minor.

The invention is illustrated in more detail by the examples which follow.

EXAMPLE 1

20 g (=0.072 mol) of triphenylphosphine oxide and 40 g (=0.291 mol) of phosphorus trichloride were kept in a sealed tube at about 360° C. for about 20 hours. After distillation in vacuo (without a column), in addition to unreacted phosphorus trichloride 29 g of a distillate were obtained which had the following composition on the basis of a $^{31}P$ NMR spectrum:
  17.1% by weight of diphenylphosphinyl chloride
  20.3% by weight of phenylphosphonyl dichloride
  3.4% by weight of triphenylphosphine oxide
  52.5% by weight of dichlorophenylphosphine
  4.1% by weight of chlorodiphenylphosphine and
  2.6% by weight of triphenylphosphine.

The conversion being 95%, the yield was 31% according to equation A above and 45% according to equation B. Thus, leaving out of account the chlorodiphenylphosphine which was produced in minor amounts, the total yield was 76% of theory.

A series of other examples (Nos. 2–16) were carried out following the pattern of this example, and the details can be seen in Tables 1 and 2. The data of Example 1 have been included in the tables.

In the example which then follows (No. 17), the upper part of the temperature range of the process according to the invention was used under normal pressure.

TABLE 1

| Example No. | Starting Compound I | Amount used | Starting Compound II | Amount used | Reaction temperature | Pressure | Reaction time | Catalyst |
|---|---|---|---|---|---|---|---|---|
| 1 | $(C_6H_5)_3P=O$ | 20 g = 0.072 mol | $PCl_3$ | 40 g = 0.291 mol | ca. 360° C. | autogenous | ca. 20 hrs. | — |
| 2 | " | " | " | " | ca. 420–430° C. | " | ca. 3 hrs. | — |
| 3 | " | " | " | " | ca. 360° C. | " | ca. 80 hrs. | — |
| 4 | " | 40 g = 0.144 mol | " | 20 g = 0.146 mol | " | " | ca. 20 hrs. | 100 mg $NiBr_2$ |
| 5 | " | 20 g = 0.072 mol | " | 40 g = 0.291 mol | " | " | " | 100 mg $PbCl_2$ |
| 6 | " | " | " | " | " | " | " | 100 mg AgCl |
| 7 | " | " | " | " | " | " | " | 100 mg CuCl |
| 8 | " | " | " | " | " | " | " | 100 mg $NiBr_2$ |
| 9 | " | " | " | " | " | " | " | 100 mg $BeCl_2$ |
| 10 | " | " | " | " | " | " | " | 100 mg $BaCO_3$ |
| 11 | " | " | " | " | ca. 420–430° C. | " | ca. 2 hrs. | 100 mg AgCl |
| 12 | " | " | $C_6H_5PCl_2$ | 40 g = 0.224 mol | ca. 360° C. | " | ca. 20 hrs. | — |
| 13 | " | " | $(C_6H_5)_2PCl$ | 40 g = 0.181 mol | ca. 370° C. | " | ca. 2 hrs. | — |
| 14 | $(C_6H_5)_2P(O)Cl$ | 20 g = 0.085 mol | $PCl_3$ | 40 g = 0.291 mol | ca. 360–370° C. | " | " | — |
| 15 | " | " | $C_6H_5PCl_2$ | 40 g = 0.224 mol | ca. 420–430° C. | " | " | — |
| 16 | $(C_6H_5)_3P=S$ | 20 g = 0.068 mol | $PCl_3$ | 40 g = 0.291 mol | ca. 430° C. | " | ca. 20 hrs. | 100 mg $BeCl_2$ |

TABLE 2

| Example No. | Amount | Reaction products (distillate) Composition (% = % by weight) | | | | | | Yield |
|---|---|---|---|---|---|---|---|---|
| | | $(C_6H_5)_2P(O)Cl$ | $C_6H_5P(O)Cl_2$ | $(C_6H_5)_3P=O$ | $C_6H_5PCl_2$ | $(C_6H_5)_2PCl$ | $(C_6H_5)_3P$ | (1) |
| 1 | 29 g | 17.1% | 20.3% | 3.4% | 52.5% | 4.1% | 2.6% | |
| 2 | 31 g | 8.0% | 26.2% | — | 62.9% | 2.2% | — | |
| 3 | 32 g | 10.8% | 25.9% | — | 59.3% | 2.9% | — | |
| 4 | 49 g | 32% | 10.4% | 5.2% | 35.8% | 11.6% | 5.0% | |
| 5 | 29 g | 6.4% | 23.8% | — | 66.6% | 3.2% | — | |
| 6 | 30.5 g | 8.6% | 22.4% | — | 64.2% | 3.1% | 0.3% | |
| 7 | 29 g | 8.8% | 23.1% | — | 62.9% | 3.9% | — | |
| 8 | 31 g | 10.6% | 22.7% | — | 61.7% | 4.8% | — | |
| 9 | 28 g | 14.1% | 19.3% | — | 60.4% | 4.3% | 1.2% | |
| 10 | 30 g | 12.4% | 20.1% | — | 60.3% | 3.7% | 1.0% | |
| 11 | 30 g | 15.9% | 20.9% | — | 54.4% | 5.2% | 1.3% | |
| 12 | 54 g | 20.4% | 2.9% | — | 43.5% | 28.2% | 4.1% | (2) |
| 13 | 52 g | 17.0% | 7.2% | 0.8% | 5.6% | 38.8% | 30.1% | (3) |
| 14 | 22 g | 33.3% | 32.3% | — | 32.4% | 1.5% | — | (4) |
| 15 | 40 g | 26.6% | 11.3% | 0.6% | 40.9% | 16.9% | 0.7% | (5) |
| | | $(C_6H_5)_2P(S)Cl$ | $C_6H_5P(S)Cl_2$ | $(C_6H_5)_3P=S$ | $C_6H_5PCl_2$ | $(C_6H_5)_2PCl$ | $(C_6H_5)_3P$ | |
| 16 | 25 g | 23.7% | 15.1% | — | 53.6% | 1.0% | — | (6) |

EXAMPLE 17

100 g (=0.513 mol) of phenylphosphonyl dichloride and 200 g (=1.45 mol) of phosphorus trichloride were mixed. This mixture was introduced dropwise, over the course of 3 hours, into a vertical quartz tube which was 60 cm long, filled with 6 mm diameter quartz Raschig rings, was flushed with nitrogen and was located in an electric oven heated to 600° C. The reaction mixture collecting in the trap was again introduced dropwise, over the course of 2 hours, into the quartz tube at 600° C. The reaction mixture now produced was distilled in vacuo. Apart from unreacted phosphorus trichloride and phosphorus oxychloride, 80 g of a distillate were obtained which, on the basis of a $^{31}P$ NMR spectrum, had the following composition:

77.9% by weight of phenylphosphonyl dichloride
15.5% by weight of dichlorophenylphosphine.

The conversion being 36%, the yield according to equation I was 38% of theory.

The figures in the column "Yield" have the following meanings:

(1) Conversion 95%, yield 31% according to equation A, and 45% according to equation B; total yield (leaving out of account the chlorodiphenylphosphine produced in minor amounts) 76% of theory (2) Yield of chlorodiphenylphosphine according to equation D 96% of theory (3) Yield of triphenylphosphine according to equation E 83.5% of theory (4) Yield according to equation F 75% of theory, conversion 63%

(5) Yield of chlorodiphenylphosphine according to equation G, at about 50% conversion, 73% of theory (6) Total yield 60% of theory.

I claim:

1. A process for the preparation of phenyl phosphorus-chlorine compounds which comprises reacting phosphine oxides or sulfides of the formula I

in which X=O or S, and m=1, 2 or 3, with phosphorus-chlorine compounds of the formula II

in which n=1, 2 or 3, at temperatures between about 330° and 700° C., the resulting phenyl phosphorus-chlorine compounds being mixtures of compounds derived from the formula I compounds by substitution of one or more $C_6H_5$ groups by chlorine and from the formula II compounds by substitution of one or more chlorine atoms by $C_6H_5$ groups.

2. The process as claimed in claim 1, wherein triphenylphosphine oxide $(C_6H_5)_3PO$ is used as the compound of the formula I, and phosphorus trichloride $PCl_3$ is used as the compound of the formula II.

3. The process as claimed in claim 1, wherein the compounds of the formulae I and II are employed in a molar ratio of about 1:1 to 1:4.

4. The process as claimed in claim 1, wherein the reaction in the temperature range between about 330° and 500° C. is carried out under elevated pressure, in particular under autogenous pressure.

5. The process as claimed in claim 1, wherein the reaction in the temperature range between about 500° and 600° C. is carried out under normal pressure.

6. The process, as claimed in claim 1, wherein X is O.

* * * * *